United States Patent [19]
Cusack

[11] Patent Number: 5,529,581
[45] Date of Patent: Jun. 25, 1996

[54] LANCET DEVICE FOR CREATING A SKIN INCISION

[75] Inventor: Robert Cusack, Edison, N.J.

[73] Assignee: International Technidyne Corporation, Edison, N.J.

[21] Appl. No.: 243,276

[22] Filed: May 17, 1994

[51] Int. Cl.⁶ .......................... A61B 17/32; A61B 10/00
[52] U.S. Cl. ...................... 606/181; 606/172; 128/753
[58] Field of Search ............................ 606/172, 171, 606/181–184, 167; 128/637, 770, 753–754

[56] References Cited

U.S. PATENT DOCUMENTS

| | | | |
|---|---|---|---|
| 4,025,696 | 5/1977 | Tucholski et al. | 426/61 |
| 4,438,770 | 3/1984 | Unger et al. | 128/637 |
| 4,462,405 | 7/1984 | Ehrlich | 606/182 |
| 4,535,769 | 8/1985 | Burns | 606/182 |
| 4,553,541 | 11/1985 | Burns | 424/1.65 |
| 4,616,694 | 10/1986 | Burns | 606/182 |
| 4,643,189 | 2/1987 | Mintz | 606/182 |
| 4,653,513 | 3/1987 | Dombrowski | 128/765 |
| 4,658,821 | 4/1987 | Chiodo et al. | 606/182 |
| 4,738,261 | 4/1988 | Enstrom | 606/182 |
| 4,817,603 | 4/1989 | Turner et al. | 606/182 |
| 4,844,095 | 7/1989 | Chiodo et al. | 606/182 |
| 4,976,704 | 12/1990 | McLees | 604/265 |
| 4,990,154 | 2/1991 | Brown et al. | 606/182 |
| 5,064,411 | 11/1991 | Gordon, III | 504/48 |
| 5,100,427 | 3/1992 | Crossman et al. | 606/182 |
| 5,105,823 | 4/1992 | Blum | 128/754 |
| 5,201,324 | 4/1993 | Swierczek | 606/182 X |
| 5,207,668 | 5/1993 | Rosen et al. | 604/272 |
| 5,212,879 | 5/1993 | Biro et al. | 29/437 |
| 5,304,192 | 4/1994 | Crouse | 606/181 |
| 5,318,581 | 6/1994 | Sunmo | 606/184 X |
| 5,370,654 | 12/1994 | Abidin et al. | 606/182 |
| 5,383,885 | 1/1995 | Bland | 606/182 |

*Primary Examiner*—Michael H. Thaler
*Attorney, Agent, or Firm*—Plevy & Associates

[57] ABSTRACT

A lancet device and associated method used for obtaining a blood sample from a patient. The lancet includes a safety housing adapted to be placed against some area of the patient's skin, such as a finger. A slotted aperture is formed through the safety housing in the region of the housing placed against the skin. An invertible spring member is disposed within the safety housing. The invertible spring member is a curved structure that automatically inverts into a generally oppositely curved orientation when the invertible spring member is flattened by a predetermined degree. The cutting blade used to make the incision is coupled to the invertible spring member within the safety housing. A manipulative element supports the invertible spring member and blade within the safety housing. The manipulative element is held at a set position in relation to the safety housing until a threshold force is applied to the manipulative element. Once the threshold force is applied, the manipulative element rapidly advances into the safety housing pushing the spring member and the blade against the wall of the safety housing that is positioned on the patient's skin. The blade extends through the slotted aperture in the safety housing and makes the desired incision. The spring member is then flattened in between the housing and the advancing manipulative element. Accordingly, the spring member is caused to change into its inverted configuration which retracts the blade permanently back into the safety housing.

17 Claims, 2 Drawing Sheets

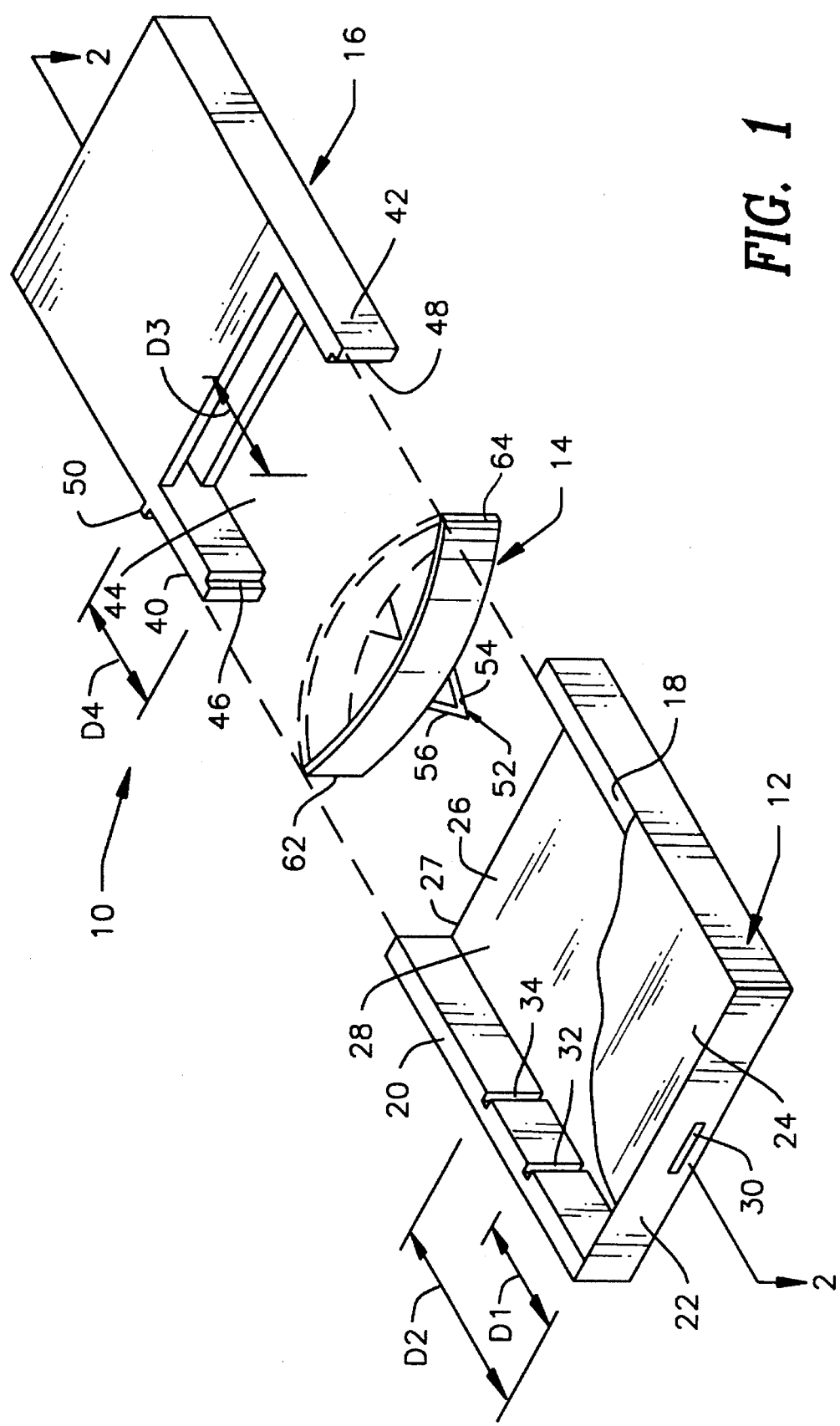

LANCET DEVICE FOR CREATING A SKIN INCISION

BACKGROUND OF THE INVENTION

I. Field of the Invention

The present invention relates to devices used in producing a skin incision for the purposes of obtaining a blood sample from a patient. More particularly, the present invention relates to disposable, one-time-use lancet devices that extend a blade from a protective housing and retract the blade back into the housing after the incision has been made.

II. Prior Art Statement

Blood samples are routinely drawn from a patient for use in various types of blood tests. The blood is usually taken from an appropriate area, such as the patient's fingertip. A series of mechanical devices for producing skin incisions necessary to draw blood samples have been developed. One such device is a reusable mechanical device that has a disposable blade. To its advantage, the mechanical device prevents the patient from seeing the often unsettling scene of his skin being cut. Further, the mechanical device provides good control of the incision. However, handling of the blades during disposal presents a danger. There is the danger of being cut by the exposed edge. Further, the health problems posed by used blades are apparent. More recent health considerations, including the possibility of contracting the AIDS virus from disposed blades, have increased the need for safer devices.

Recognizing the dangers presented by used lancet devices, numerous prior art devices have been developed that automatically retract a blade into a safety housing after the incision is made. This prevents further contact with the blade and eliminates the problem of the blade accidentally cutting another. Such prior art devices therefore typically include a cutting blade, a safety housing, a means to project the cutting blade out of the housing, a means to retract the blade back into the housing and a triggering device. Accordingly, such prior art lancet devices tend to have complex workings that are expensive to manufacture, difficult to assemble and are hard to use. Examples of such prior art are shown by U.S. Pat. No. 3,760,809 to Campbell, entitled SURGICAL LANCET HAVING CASING; U.S. Pat. No. 4,064,871 to Reno, entitled DEVICE FOR MAKING PRECISE INCISIONS FOR BLEEDING TIME TESTING AND THE LIKE; and U.S. Pat. No. 4,157,086 to Maiorano et al, entitled APPARATUS FOR PROVIDING SKIN CUTS TO A PREDETERMINED MEASURE.

Since one-time-use lancet devices are designed to be disposable after one use, it will be understood that the manufacturer with the lowest unit price would have an advantage over competitors. Consequently, manufactures have been motivated to design disposable lancets with simpler designs that can be made less expensively. In response to such design efforts, manufactures have developed lancets with only two or three separate parts. In such devices a cutting blade is held by a complex molded structure that both advances and retracts the blade. Such prior art is exemplified by U.S. Pat. No. 4,553,541 to Burns, entitled AUTOMATIC RETRACTABLE LANCET ASSEMBLY, and U.S. Pat. No. 5,212,879 to Biro et al., entitled METHOD FOR MANUFACTURING A DISPOSABLE-RETRACTABLE FINGER STICK DEVICE, which is assigned to International Technidyne Corp, the assignee herein. Although such devices have far less parts than some prior art lancet devices, they are no less complex. Accordingly, the tools needed to mold the primary lancet structure is highly complex and the parts produced must be maintained at high tolerances. This produces a large amount of reject parts and significant downtime as the molding tool is cleaned and maintained. All this work adds to the cost of the lancet device and makes it difficult to consistently produce a high quality product.

It is therefore an object of the present invention to provide a disposable lancet that is relatively inexpensive to manufacture and not requiring complex molded parts.

It is a further object of the present invention to provide a disposable lancet that is easy to use and highly consistent in its operation.

SUMMARY

The present invention is a lancet device and the associated method used for obtaining a blood sample from a patient. The lancet includes a safety housing adapted to be placed against some area of the patient's skin, such as a finger. A slotted aperture is formed through the safety housing in the region of the housing placed against the skin. An invertible spring member is disposed within the safety housing. The invertible spring member is a curved structure that automatically inverts into a generally oppositely curved orientation when the invertible spring member is flattened by a predetermined degree. The cutting blade used to make the incision is coupled to the invertible spring member within the safety housing.

A manipulative element supports the invertible spring member and blade within the safety housing. The manipulative element is held at a set position in relation to the safety housing until a threshold force is applied to the manipulative element. Once the threshold force is applied, the manipulative element rapidly advances into the safety housing pushing the spring member and the blade against the wall of the safety housing that is positioned on the patient's skin. The blade extends through the slotted aperture in the safety housing and makes the desired incision. The spring member is then flattened in between the housing and the advancing manipulative element. Accordingly, the spring member is caused to change into its inverted configuration which retracts the blade permanently back into the safety housing.

BRIEF DESCRIPTION OF THE DRAWINGS

For a better understanding of the present invention, reference is made to the following description of an exemplary embodiment thereof, considered in conjunction with the accompanying drawings, in which:

FIG. 1 is an explode perspective view of one preferred embodiment of the present invention;

DETAILED DESCRIPTION OF THE PRESENT INVENTION

Figure 2A:
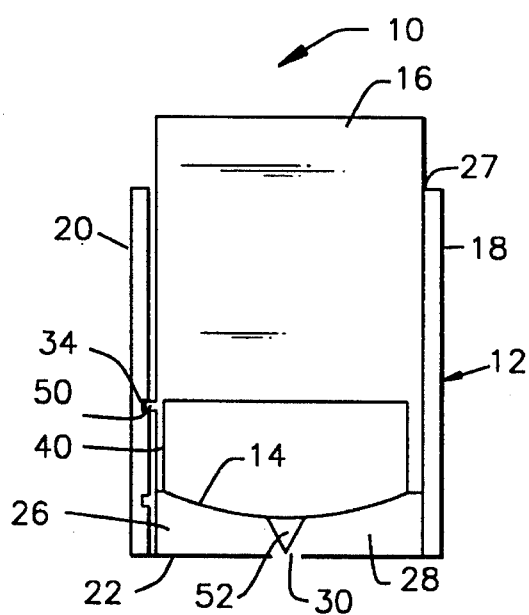
FIG. 2a is a cross-sectional view of the embodiment shown in FIG. 1, viewed along section line 2—2, wherein the present invention is shown prior to use.

Referring to FIG. 1 there is shown one preferred embodiment of the present invention lancet device 10. The lancet device 10 is comprised of three parts, namely a safety housing 12, an invertible spring element 14 and a spring support member 16.

The safety housing 12 includes a right wall member 18, a left wall member 20, and a facewall member 22 that define the peripheral shape of the housing 12 in between a top wall member 24 and a bottom wall member 26. There is no wall opposite the facewall member 22. As such, the housing 12 is a narrow box-like structure having one open end—27, wherein the housing 12 defines a central cavity 28 that communicates with the exterior of the housing 12 via the open end 27. A slotted aperture 30 is disposed in the facewall member 22 opposite the open end 27. The slotted aperture 30 extends completely through the facewall member 22, thereby communicating with the central cavity 28 within the housing 12. Two slots 32, 34 are disposed within the left wall member 20. The slots 32, 34 extend from the top wall member 24 to the bottom wall member 26 and serve a purpose which will be later described. The first slot 32 is located a first predetermined distance D1 away from the interior surface of the facewall member 22, while the second slot 34 is located a second predetermined distance D2 away from the interior surface of facewall member 22.

The spring support member 16 is sized to fit within the open end 27 of the safety housing 12. The spring supporter member 16 includes two support arm elements 40, 42 that define an open ended relief 44 within the spring supporter member 16. The relief 44 is rectangular in shape, having depth D3 from the forward most end of the support arm elements 40, 42. A stepped ledge 46, 48 is disposed on the first and second support arm elements 40, 42, respectively. The stepped ledges 46, 48 face each other across the open ended relief 44. A locking projection 50 extends from the side of the trigger member 16. The locking projection 50 is located a distance D4 from the end of the first support arm element 40. For reasons which will be later explained, the distance D4 between the locking projection 50 and the end of the first support arm element 40 is equal to the distance D1 between the first slot 32 and the inside surface of the facewall member 22, within the safety housing 12. Similarly, the locking projection 50 is sized to fit within either the first slot 32 of the second slot 34 formed within the safety housing 12.

The invertible spring element 14 is a piece of metal that is curved in a first direction. A triangular blade 52 is bent at a perpendicular to the remainder of the spring element 14 proximate the apex of the curve. The blade 52 has two highly sharpened edges 54, 56 that enable the blade to quickly and easily pierce skin and draw blood. The spring element 14 is constructed so that should the spring element 14 be flattened by a force applied to the blade 52, the spring element 14 automatically inverts into a oppositely curved orientation (shown in hidden lines) whereby the blade 52 descends below the apex of the curve. The purpose of the invertible nature spring element 14 will be later explained. The spring element 14 has two short ends 62, 64 that rest within the stepped ledges 46, 48 on the support arm elements 40, 42. The stepped ledges 46, 48 retain the short ends 62, 64 of the spring element 14 a predetermined distance apart while the spring element 14 is curved in the direction shown.

Referring to FIG. 2a the present invention lancet device 10 is shown in an assembled condition, prior to use. As can be seen, the spring support member 16 fits within the cavity 28 defined by the safety housing 12, wherein the spring support member 16 passes through the open end 27 of the safety housing 12. The spring support member 16 is sized to generally conform to the size of the cavity 28 into which it passes. Accordingly, the spring support member 16 abuts against the right wall member 18, left wall member 20, top wall member 24 (not shown) and bottom wall member 26 when placed within the safety housing 12. This limits the lateral movement of the spring support member 16 in relation to the safety housing 12, thereby enabling movement of the spring support member 16 only in a direction toward the facewall member 22 of the safety housing 12.

In FIG. 2a the lancet device 10 is shown prior to use. In this condition, the locking projection 50 that extends from the side of the spring support member 16 is engaged within the second slot 34 formed within the left wall member 20 of the safety housing 12. The distance D4 (FIG. 1) from the end of the first support element 40 to the locking projection 50 and the distance D2 (FIG. 1) from the face surface member 22 to the second slot 34 are proportioned so that the blade 52 does not extend through the slotted aperture 30 in the face surface member 22 when the locking projection 50 is in the second slot 34.

Figure 2B:
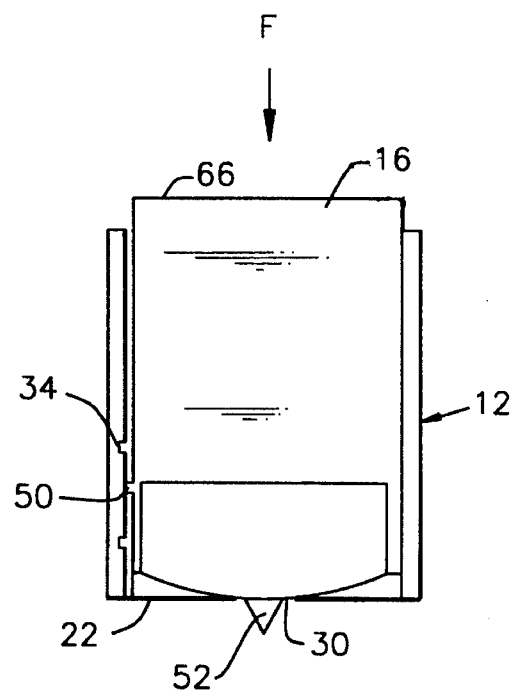
FIGS. 2b and 2c is a cross-sectional views of the embodiment shown in FIG. 1, viewed along section line 2—2, wherein the present invention is shown making an incision during use.

Referring to FIG. 2b it will be seen that when a force F is applied to the top surface 66 of the spring support member 16 in a direction that drives the spring support member 16 into the safety housing 12, the locking projection 50 can be biased out of the second slot 34. In the preferred embodiment, the safety housing 12 is made of a plastic material that would bow under the pressure of the locking projection 50 when a predetermined threshold force F is transferred to the locking projection 50. In other words, as a force is applied to the spring support member 16, the force is experienced by the locking projection 50 as the locking projection 50 is biased out of the second slot 34. As the force experienced by the locking projection 50 builds, the locking projection 50 causes the left wall member 20 and/or the spring support member 16 to bow. When the applied force F reaches a predetermined level, the locking projection 50 disengages the second slot 34 and the previously stored energy is suddenly released. As such, the spring support member 16 suddenly and rapidly begins to travel into the safety housing in the direction of force F.

As the spring support member 16 moves into the safety housing 12, the blade 52 is pushed through the slotted aperture 30 in the facewall member 22 of the safety housing 12. Accordingly the blade 52 temporarily extends out of the housing 12, enabling the blade 50 to make an incision. Once the blade 52 has completely extended through the slotted aperture 30, the invertible spring element 14 contacts the facewall member 22. The advancement of the invertible spring element 14 against the facewall member 22 causes the invertible spring element 14 to deform and flatten.

Figure 2C:
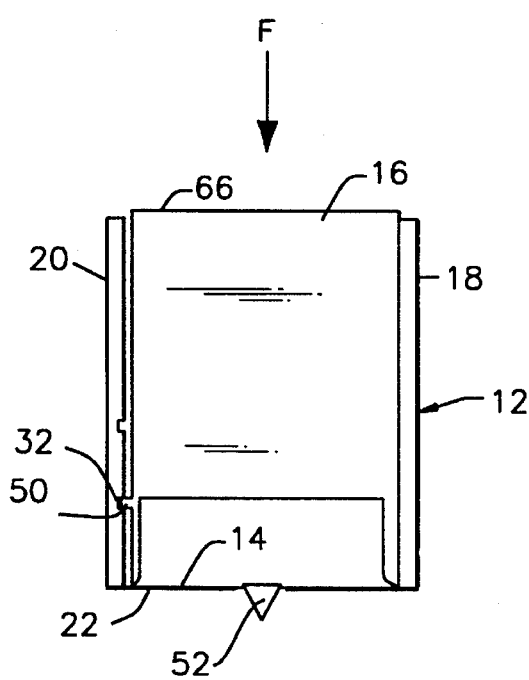

Referring to FIG. 2c it can be seen that the spring support member 16 continues to advance into the safety housing 12 until the locking projection 50 passes into the first slot 32 on the left wall member 20. At this point, the stored energy is partially dissipated and the safety housing 12 is less apt to bow. Consequently, the locking projection 50 becomes locked into place within the first slot 32, despite the presence of force F still being applied to the top surface 66 of the spring support member 16.

Figure 2D:
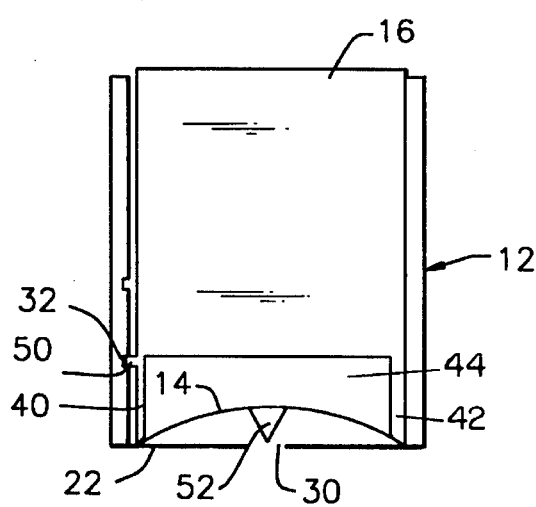
FIG. 2d is a cross-sectional view of the embodiment shown in FIG. 1, viewed along section line 2—2, wherein the present invention is shown having the blade retracted after an incision has been made.

The locking projection 50 engages the first slot 32 at a point corresponding to when the invertible spring element 14 is generally flattened against the facewall element 22 of safety housing 12. Referring to FIG. 2d, it can be seen that once the spring element 14 is flattened, the spring element 14 automatically inverts into an oppositely curved orientation. The inverted spring element 14, therefore bends backward into the open ended relief 44 defined between the support arm elements 40, 42 of the spring support member 16. Once inverted the distance between the apex of the curved spring element 14 and the facewall member 22 is greater than the height of the blade 52. Consequently, as the spring element 14 snaps into its inverted configuration, the blade 52 is quickly withdrawn back into the safety housing 12.

Once used, and the spring element 14 becomes inverted, the present invention lancet device 10 cannot be used again. The locking projection 50 of the spring support member 16 is set within the first slot 32 in the safety housing 12. Accordingly, the spring support member 16 cannot be removed from the safety housing 12. Since the spring support member 16 cannot be removed, the spring element 14 cannot be accessed. As a result, the spring element 14 cannot be reinverted to its original configuration. Consequently, the blade 52 remains at an orientation where the blade 52 is physically incapable of again extending out of the safety housing.

It is understood that the embodiment described herein is merely exemplary and that a person skilled in the art may make to the size, shape and orientations of the described components. For example, the device need not be shaped as shown, but may have another shape, such as a cylinder where the invertible spring element has a hemispherical shape. All such variations and modifications are intended to be included within the spirit and scope of the present invention, as defined by the appended claims.

What is claimed is:

1. A lancet device, comprising:

a housing having an aperture disposed through one surface thereof;

an invertible spring element having a first surface and an opposite second surface, wherein said spring element generally follows a predetermined radius of curvature and has an apex, said spring element being invertible between two at rest orientations that include a first curved orientation, wherein said apex is disposed on said first surface and an opposite second curved orientation, wherein said apex is disposed on said opposite second surface, whereby said spring element automatically changes between said first orientation and said second orientation when a predetermined force is applied to said apex that acts to flatten said spring element;

a blade coupled to said invertible spring element;

means for advancing said spring element in said housing to a first position, wherein said blade extends through said aperture, and a subsequent second position wherein said housing applies said predetermined force to said apex, thereby causing said spring element to automatically invert from said first curved orientation to said second curved orientation and retract said blade back through said aperture and into said housing.

2. The device according to claim 1, wherein said blade is unistructurally formed as part of said invertible spring element.

3. The device according to claim 1, wherein said means for advancing said spring element includes a manipulative element coupled to said invertible spring element whereby said spring element can be advanced from said first position to said second position by the advancement of said manipulative element into said housing.

4. The device according to claim 3, further including a locking means for locking said manipulative element into said housing when said spring element is at said second position, thereby preventing the reuse of said lancet device after said spring element is moved to said second position.

5. The device according to claim 3, further including a retaining means for retaining said manipulative element in a set orientation relative to said housing until a force applied to said manipulative element exceeds a predetermined threshold, wherein said manipulative element advances said spring element to said first position and said second position in rapid succession.

6. The device according to claim 3, wherein said manipulative element retains said spring element in a starting position prior to advancing said spring element to said first position, said manipulative element further including a locking projection that engages said housing and prevents said manipulative element from leaving said starting position until a predetermined threshold force is applied to said manipulative element.

7. A lancet device for creating an incision through the skin of a patient, comprising:

a housing defining an enclosure, wherein said housing includes a surface adapted to be placed upon the skin of the patient, said surface having a slotted aperture formed therethrough that communicates with said enclosure;

a manipulative element having a first region disposed within said enclosure of said housing and a second region that extends out of said housing, wherein said first region can be advanced into said housing from a first position to a second position by manually applying a predetermined force to said second region of said manipulative element;

an invertible member disposed in said housing between said slotted aperture and said manipulative element, said invertible member having a generally curved first orientation, wherein said invertible member automatically inverts to a second generally oppositely curved orientation when said first orientation is flattened to a predetermined degree between said housing and said manipulative element.

a blade coupled to said invertible member, wherein said blade is contained within said housing when said first region of said manipulative element is at said first position, and said blade is temporarily driven through said aperture in said housing when said manipulative element is driven from said first position to said second position, wherein said manipulative element flattens said invertible member by said predetermined degree at said second position and said invertible member automatically inverts from said first orientation to said oppositely curved orientation, thereby retracting said blade back into said housing.

8. The device according to claim 7, wherein a locking projection extends from said manipulative element and a first relief and a second relief are disposed on said housing within said enclosure, said locking projection engaging said first relief when said first region of said manipulative element is at said first position and said locking projection engaging said second relief when said first region of said manipulative element is at said second position.

9. The device according to claim 8, wherein said locking projection engages said first relief and retains said first region of said manipulative element at said first position until said predetermined force is applied to said manipulative element.

10. The device according to claim 8, wherein said locking projection engages said second relief when said first region of said manipulative element is at said second position, thereby preventing the movement of said manipulative element from said second position.

11. The device according to claim 7, wherein said blade is unistructurally formed as part of said invertible member.

12. The device according to claim 7, wherein said invertible member has a peripheral edge and said manipulative elements contacts said invertible member at a plurality of points along said peripheral edge, whereby said invertible member is advanced in said housing as said manipulative element is advanced in said housing.

13. A method of creating an incision in a person's skin, comprising the steps of:

providing an invertible structure maintained in a safety housing, that automatically inverts between a first curved geometry and an oppositely curved geometry when said invertible structure is flattened to a predetermined degree, wherein said structure has a blade coupled thereto, said blade being the most distal point of said invertible structure when said invertible structure is in said first curved geometry and said blade not being the most distal point when said invertible structure is in said oppositely curved geometry;

placing said safety housing against the person's skin;

advancing said invertible structure in said first geometry against a surface within said safety housing, which step further includes the substep of coupling said invertible structure to a manipulative element and advancing said manipulative element within said safety housing;

projecting said blade through an aperture formed through said surface of the safety housing, whereby said blade extends out of the safety housing and creates an incision;

flattening said invertible structure by said predetermined degree, causing said invertible structure to invert into said oppositely curved geometry from said first curved geometry, thereby retracting said blade out of the person's skin; and locking said invertible structure within said safety housing, thereby preventing said invertible structure from being reinverted to said first geometry and used again.

14. The method according to claim 13, wherein said step of causing said invertible structure to invert includes compressing said invertible structure between said manipulative element and said safety housing, thereby flattening said invertible structure by said predetermined degree and inverting said invertible structure from said first curved geometry into said oppositely curved geometry.

15. The method according to claim 13, wherein said invertible structure is metal and said blade is unistructurally formed as part of said invertible structure.

16. The method according to claim 13, further including the step of retracting said blade into said safety housing as said invertible structure inverts into said oppositely curved geometry.

17. The method according to claim 13, wherein said step of advancing said invertible structure includes retaining said invertible structure into a set position; applying a force to said invertible structure; and releasing said invertible structure from said set position when said force exceeds a predetermined threshold force.

\* \* \* \* \*